United States Patent

Johnson

[11] 4,031,131
[45] June 21, 1977

[54] PROCESS FOR PREPARING PHENOXYBENZOIC ACIDS

[75] Inventor: Wayne O. Johnson, Warminster, Pa.

[73] Assignee: Rohm and Haas Company, Philadelphia, Pa.

[22] Filed: Sept. 29, 1975

[21] Appl. No.: 617,561

[52] U.S. Cl. .................. 260/473 G; 260/520 R
[51] Int. Cl.² ............................. C07C 69/76
[58] Field of Search ........ 260/473 R, 520 R, 473 G

[56] References Cited

OTHER PUBLICATIONS

C. R. Noller, Chemistry of Organic Compounds, (2nd Ed.), W. B. Saunders Co., Philadelphia.

*Primary Examiner*—Paul J. Killos
*Attorney, Agent, or Firm*—William E. Lambert, III

[57] ABSTRACT

Phenoxybenzoic acids and esters of the formula

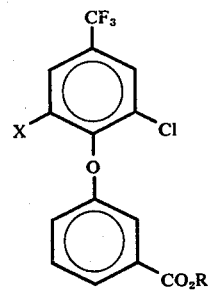

wherein R is hydrogen or alkyl and X is hydrogen or chlorine can be prepared by reacting the disalt of 3-hydroxybenzoic acid with a 3-chloro-4-halobenzotrifluoride. These phenoxybenzoic acids and esters can then be selectively nitrated to give the corresponding 2-nitro-5-(substituted)phenoxybenzoic acids and esters. The nitrated esters can also be prepared by first nitrating the corresponding acid and then esterifying with an appropriate alcohol.

10 Claims, No Drawings

PROCESS FOR PREPARING PHENOXYBENZOIC ACIDS

This invention relates to a novel process for preparing certain phenoxybenzoic acids which have herbicidal activity or which are intermediates in preparing herbicides.

In U.S. Pat. No. 3,798,276, granted on Mar. 19, 1974 and U.S. patent application Ser. No. 331,719, filed on Feb. 12, 1973, both by Bayer et al, a useful class of diphenyl ester herbicides is disclosed. However, certain of these compounds, having the formula

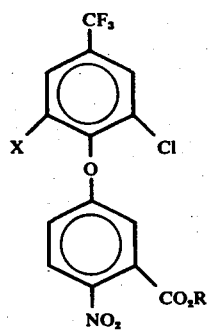

(I)

wherein X is a hydrogen atom or a chlorine atom, and R is a hydrogen atom or a ($C_1$–$C_4$) alkyl group, while having high herbicidal activity are difficult to prepare by conventional methods. For example, when the corresponding 3-cyano diphenyl ether is hydrolyzed with aqueous acid, hydrolysis of the -$CF_3$ group can also occur. Moreover, no significant reaction occurs between 2-chloro-4-trifluoromethyl phenol and methyl 5-chloro-2-nitrobenzoate. Thus, new methods to produce the compounds of Formula I have been needed. A new synthetic route to these compounds using 3-hydroxybenzoic acid and a 3-chloro-4-halobenzotrifluoride has now been found.

According to the invention, in the first step in preparing the compounds of Formula I, phenoxybenzoic acids of the formula

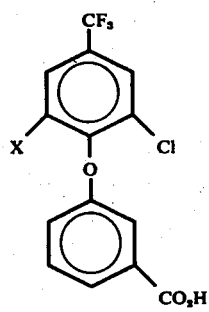

(II)

wherein X is as defined above, are prepared by reacting 3-hydroxybenzoic acid with at least two equivalents of an inorganic base to form the disalt of the 3-hydroxybenzoic acid. The disalt is then reacted with a benzotrifluoride of the formula

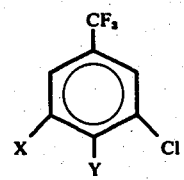

(III)

wherein Y is a chlorine atom or a fluorine atom and, X is as defined above. Unexpectedly, although the benzotrifluoride is highly insoluble in aqueous media and the disalt is highly insoluble in nonaqueous media, reaction between these two compounds does occur in highly polar aprotic organic solvents. The acid of Formula II is then generated by acidifying with a strong inorganic acid the product formed from the benzotrifluoride and the disalt.

The disalt is generally prepared in a polar organic solvent such as methanol or dimethylsulfoxide at a temperature of about 0° to about 150° C. However, when a protic solvent such as methanol is used, the solvent is removed, for example, by evaporation or distillation, thus isolating the disalt, prior to reaction with the benzotrifluoride in a polar aprotic solvent. The disalt can also be prepared using aqueous base, followed by isolation of the disalt, generally by adding the polar aprotic organic solvent together with a solvent such as toluene, which when heated will remove the water as an azeotrope. After removal of the water, the disalt can be used directly in solution for reaction with the benzotrifluoride.

Any moderately strong to strong inorganic base can be used to generate the disalt. Typical bases include sodium hydroxide, potassium hydroxide, sodium carbonate, potassium carbonate, or the like. Generally, at least two equivalents of the base are used. While an excess of the hydroxide may not be desirable, an excess of the carbonate can be used.

The reaction between the disalt and the benzotrifluoride is generally carried at a temperature of about 100° to about 180° C., using equimolar amounts of the disalt and benzotrifluoride. A slight excess of the disalt may be advantageous in helping to insure completion of the reaction. Among the polar aprotic organic solvents which can be used are dimethylsulfoxide, dimethylformamide, sulfolane, N-methyl-2-pyrrolidone, hexamethylphosphoric triamide, and the like, or mixtures of such solvents.

The reaction between the disalt and the benzotrifluoride produces a salt of the desired acid of Formula II. The free acid can be generated by reacting the salt with a strong inorganic acid, such as hydrochloric acid, nitric acid, or the like. One convenient method to produce and isolate the free acid involves pouring the dissolved reaction product of the disalt and benzotrifluoride into water, extracting this aqueous mixture with a nonpolar organic solvent, such as carbon tetrachloride, methylene dichloride, ethylene dichloride, perchloroethylene, chloroform, toluene, hexane, or the like, to remove unreacted benzotrifluoride, adding the strong acid to the aqueous mixture to precipitate the free acid, and removing the free acid, for example by filtration or extraction by a nonpolar organic solvent.

The second step in preparing the compounds of Formula I involves nitrating compounds of the formula

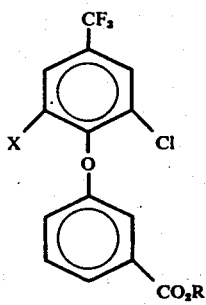

(IV)

wherein X and R are as defined above. When R is a hydrogen atom, the desired product can be obtained by nitrating the corresponding acid of Formula II directly. When R is a ($C_1$–$C_4$) alkyl group, the corresponding acid of Formula II is first esterified, and then nitrated. Unexpectedly, it has been found that the nitration reaction of either the acid of ester gives overwhelmingly the 4-nitro compound, rather than a difficulty separable mixture of the 4-nitro compound and the 6-nitro compound.

The nitration reaction, of either the acid or the ester, is generally carried out at a temperature of about 0° to about 70° C. Any conventional electrophilic nitrating agent can be used. However, the preferred nitrating agents include nitric acid/sulfuric acid, potassium nitrate/sulfuric acid, or nitric acid/sulfuric acid/acetic anhydride. An optional cosolvent, such as methylene dichloride, ethylene dichloride, chloroform, perchloroethylene, or the like can also be used. The cosolvent can be the same as used to isolate the free acid used as the starting reagent.

When R of Formula I is a ($C_1$–$C_4$) alkyl group, it is generally preferred to carry out the esterification of the acid of Formula II prior to the nitration reaction. Essentially any conventional esterification technique can be used to prepare the esters of Formula IV. For example, the acid chloride of an acid of Formula II can be prepared by reacting the acid with a chlorinating agent such as thionyl chloride, phosphorous oxychloride, phosphorous pentachloride, oxalyl chloride, or the like in an inert solvent, such as a hydrocarbon, a chlorinated hydrocarbon, an ester, or the like, at a temperature of about 0° C. to the reflux temperature of the solvent. An excess of the chlorinating agent can be used, but such excess is generally removed prior to the esterification reaction itself. The acid chloride is then reacted with a molar or excess amount of the appropriate ($C_1$–$C_4$) alkanol. In another useful esterification route, the acid of Formula II is reacted directly with a ($C_1$–$C_4$) alkanol under anhydrous conditions, using an anhydrous acid or dehydrating agent, such as hydrochloric acid, sulfuric acid, phosphorous pentoxide, or the like, as a catalyst. The reaction can conveniently be carried out using the alkanol itself as the solvent, but an inert cosolvent can also be used. The reaction is usually run at a temperature of about 0° C. to the reflux temperature of the solvent. In each of the two esterification procedures described above, the free acid itself is used as the starting reagent. However, the ester can be prepared directly from the acid salt, as dissolved in the polar aprotic organic solvent, by using an alkylating agent such as methyl sulfate, methyl bromide, ethyl bromide, ethyl chloride, or the like. The ester of Formula IV can be nitrated without isolation, if an appropriate solvent is used for the esterification reaction, or it can be isolated, for example by distillation or evaporation of the esterification solvent or other conventional techniques, prior to the nitration.

The acids of Formula I can also be prepared by hydrolysis of the esters of Formula I. The hydrolysis reaction can be effected by any conventional acid- or base-catalyzed hydrolysis technique, or by transesterification of the ester with an organic acid such as formic acid, acetic acid, or other appropriate lower alkanoic acid.

The following examples will further illustrate the invention, but are not intended to limit it in any way.

EXAMPLE 1

Preparation of 3-(2-Chloro-4-trifluoromethylphenoxy)benzoic acid

METHOD 1

To a loosely stoppered 500 ml single-necked flask is charged methanol (250 ml) and potassium hydroxide pellets (85%, 13.2 g. 0.20 mole). When the exotherm has subsided and all the potassium hydroxide is in solution, 3-hydroxybenzoic acid (13.8 g. 0.10 mole) is charged rapidly. After stirring for 10 minutes, the methanol is removed in vacuo and the white glassy solid (21.4 g.) is scraped from the flask (in a glove bag through which nitrogen is flowing) and used directly.

To a 300 ml. 3-necked flask fitted with a magnetic stirring bar, condenser, drying tube and thermometer is charged the solid from above, dimethylsulfoxide (100 ml), 3,4-dichlorobenzotrifluoride (21.5 g. 0.10 mole) and anhydrous potassium carbonate (5.0 g.) to assure an alkaline pH. The reaction temperature is taken rapidly to 138°–44° C. while vigorous stirring is maintained. After 4 hours a significant conversion is realized and heating is continued overnight (total 22 hrs.). The reaction mixture is then cooled to room temperature and poured into water (1000 ml) and the aqueous reaction mixture extracted with $CCl_4$ (200 ml). The aqueous layer is then decanted and acidified to pH1 with concentrated hydrochloric acid. The white solid that precipitates is collected by filtration and vacuum dried at 60° C. overnight to give 27 g. of an off-white solid 3-(2-chloro-4-trifluoromethylphenoxy)benzoic acid (85% yield), mp 124°–5° C.

METHOD 2

To a 300 ml, 3-necked flask equipped with a condenser, stirrer, drying tube and thermometer is charged dimethylsulfoxide (100 ml), anhydrous potassium carbonate (30 g. >0.20 mole), 3,4-dichlorobenzotrifluoride (21.5 g., 0.10 mole), pinacol (10 g.) and 3-hydroxybenzoic acid (13.8 g., 0.10 mole). The reaction temperature is then taken slowly to 140°–5° C. while stirring vigorously and maintained as such for 4 days. The reaction mixture is then cooled to room temperature and the inorganic solids removed by filtration prior to pouring the filtrate into water (1200 ml). The aqueous solution is then triturated with $CCl_4$ (2 × 200 ml), decanted and then acidified to pH1 (conc. HCl) to give a tan colored solid, 25,6 g., mp 114°–17° C. This solid is further purified by dissolving in $CCl_4$ (500 ml) and drying with anhydrous $MgSO_4$. The $CCl_4$ solution is reduced in vacuo to give 19.6 g. (62%) of a yellow solid, mp 116°–19° C. Recrystallization of the yellow solid from hexane gives a tan colored solid, 3-(2- chloro-4-trifluoromethylphenoxy)-benzoic acid, mp 122°–3° C.

EXAMPLE 2

Preparation of 5-(2-Chloro-4-trifluoromethylphenoxy)-2-nitrobenzoic acid

METHOD 1

To a flask is charged concentrated sulfuric acid (40 ml) and ethylene dichloride (25 ml), which is then cooled (ice/salt bath) to 0° C. at which tie 3-(2-chloro-4-trifluoromethylphenoxy)benzoic acid (10.0 g. 0.315 mole) is added portion-wise. Then anhydrous potassium nitrate (3.18 g. 0.0315 mole) is added in increments over a ½hr. period at 0° C. One-half hour after the addition is completed the reaction mixture is allowed to warm gradually to room temperature, the reaction mixture is poured into 400 g. of an ice/water mixture, the aqueous mixture is then extracted with chloroform (2 × 100 ml), the chloroform/water insoluble portion removed by filtration (0.5 g.), the chloroform layer decanted and dried over anhydrous sodium sulfate and the solvent removed in vacuo to give 9.4 g. of 5(2-chloro-4-trifluoromethylphenoxy)-2-nitrobenzoic acid, mp 137°–50° C., which is recrystallized from benzene/petroleum ether, mp 151.5°–57° C.

Anal. Calcd. for $C_{14}H_7ClF_3NO_5$: C, 46.50; H, 1.95; N, 3.87; Cl, 9.80; F, 15.76.

Found: C, 46.79; H, 1.91; N, 3.65; Cl. 9.46; F, 15.35.

METHOD 2

To a 2-liter, 3-necked flask fitted with a stirrer, thermometer and addition funnel is charged methylene chloride (250 ml), 3-(2-chloro-4-trifluoromethylphenoxy)benzoic acid (158 g. 0.500 mole), acetic anhydride (152 g.), and then concentrated sulfuric acid (9.8 g.). With external cooling, a 70% nitric acid in water solution is added at a rate so as to maintain the reaction temperature at about 20° C. (1 hour period of addition). Then additional acetic anhydride (22.8 g.) is added to the reaction mixture followed by slow addition of more nitric acid (6.8 g.). The reaction mixture is then stirred at 20° C. for 1 hour, poured into 2 liters of an ice/water mixture and the solid precipitate collected by filtration and vacuum-dried at 60° C. overnight to give 83.4 g. of 5-(2-chloro-4-trifluoromethylphenoxy)-2-nitrobenzoic acid, mp 152°–6° C.

EXAMPLE 3

Preparation of Methyl 5-(2-Chloro-4-trifluoromethylphenoxy)-2-nitrobenzoate

METHOD 1 a. Esterification of 3-(2-Chloro-4-trifluoromethylphenoxy)benzoic acid

To a 300 ml, 3-necked flask equipped with a stirrer, gas bubbling tube, condenser, thermometer and drying tube is charged anhydrous methanol (100 ml) and 3-(2-chloro-4-trifluoromethylphenoxy)benzoic acid (12 g., 0.038 mole). Anhydrous hydrogen chloride gas is bubbled into the reaction mixture until the reaction temperature (exotherm) rises to 50° C. The reaction mixture is then maintained at 50° C. with external heating for 4 hours, then cooled, the solvent removed in vacuo and the residue dissolved in $CCl_4$ (200 ml) and triturated with water (50 ml). The decanted and dried (anh. $MgSO_4$) $CCl_4$ layer is reduced in vacuo to give 12.2 g. of methyl 3-(2-chloro-4-trifluoromethylphenoxy)benzoate (98% yield).

Anal. Calcd. for $C_{15}H_{10}ClF_3O_3$: C, 54.48; H, 3.05; F, 17.23; Cl, 10.72.

Found: C, 54.84; H, 3.17; F, 17.19; Cl, 10.61.

b. Nitration of Methyl 3-(2-Chloro-4-trifluoromethylphenoxy)benzoate

To a 50 ml, 3-necked fitted with a stirrer, condenser, drying tube and thermometer is charged concentrated sulfuric acid (10 ml) and then methyl 3(2-chloro-4-trifluoromethylphenoxy)benzoate (9.92 g., 0.030 mole) at room temperature. A water bath is then placed under the flask and the temperature moderated to 23.5° C. Then powdered potassium nitrate (3.11 g., 0.030 mole) is charged in eight increments at 15 minute intervals. The reaction mixture is stirred at room temperature overnight. The contents are then poured slowly onto ice (200 g.) and extracted into $CCl_4$ (2 × 100 ml). The combined $CCl_4$ extracts are dried and reduced in vacuo to give 10.7 g. of methyl 5-(2-chloro-4-trifluoromethylphenoxy)benzoate as a yellow oil (>95%) that partially solidifies on standing.

Anal. Calcd. for $C_{15}H_9ClF_3NO_5$: C, 47.50; H, 2.42, Cl, 9.45; F, 15.20; N, 3.73.

Found: C, 47.50; H, 2.38; Cl, 9.20; F, 14.65; N, 4.32.

METHOD 2

Esterification of 5-(2-Chloro-4-trifluoromethylphenoxy)2-nitrobenzoic acid

Hydrogen chloride is bubbled thru a solution of 5-(2-chloro-4-trifluoromethylphenoxy)-2-nitrobenzoic acid (2.3 g. 0.0064 mole) in methanol (50 ml.) for 10 hours at 32° C., stirred overnight and the solvent removed to give 1.5 g. of methyl 5-(2-chloro-4-trifluoromethylphenoxy)-2-nitrobenzoate.

EXAMPLE 4

Hydrolysis of Ethyl 5-(2-Chloro-4-trifluoromethylphenoxy)-2-nitrobenzoate

Ethyl 5-(2-chloro-4-trifluoromethylphenoxy)-2-nitrobenzoate (20 g. >0.058 mole) and ethanol (20 g.) are charged to a 100 ml round bottom flask. 50% NaOH (9.6 g., 0.120 mole) is added dropwise at 25° C. An exotherm ensues, the temperature rises to 52°, and the batch darkens considerably. Water (100 ml) is added, followed by sufficient 6M HCl to give a final pH of about 1. A heavy oil is separated. The aqueous acid layer is extracted with ethylene dichlorides and the combined organic layers are stripped on the rotary evaporator to give 17.6 g. of a thick brown syrup. When heated, the syrup thins and begins to crystallize. A small portion is chipped from the flask, triturated with ethylene dichloride and an off-white powder, mp 156°–160°, is recovered and identified as the desired ethyl 5-(2-chloro-4-trifluoromethylphenoxy)-2-nitrobenzoate based on melting point and nmr spectrum.

It is to be understood that changes and variations may be made without departing from the spirit and scope of the invention as defined by the appended claims.

I claim:

1. A method for preparing a compound of the formula

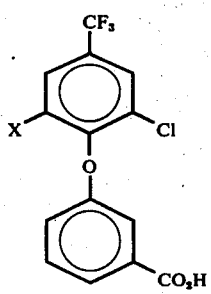

wherein X is a hydrogen atom or a chlorine atom, which comprises
 a. reacting 3-hydroxybenzoic acid with at least two equivalents of an inorganic base to form the disalt of the 3-hydroxybenzoic acid,
 b. reacting in a polar aprotic organic solvent the disalt with a benzotrifluoride of the formula

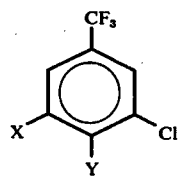

wherein Y is a chlorine atom or a fluorine atom and X is as defined above, and
 c. acidifying the product of (b) with a strong inorganic acid.

2. The method of claim 1 wherein X is hydrogen and Y is chlorine.

3. A method for preparing a compound of the formula

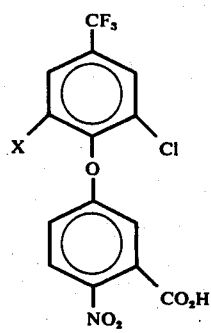

wherein X is a hydrogen atom or a chlorine atom, which comprises
 a. reacting 3-hydroxybenzoic acid with at least two equivalents of an inorganic base to form the disalt of the 3-hydroxybenzoic acid,
 b. reacting in a polar aprotic organic solvent the disalt with a benzotrifluoride of the formula

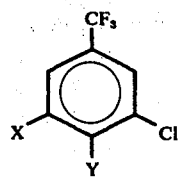

wherein Y is a chlorine atom or a fluorine atom and X is as defined above,
 c. acidifying the product of (b) with a strong inorganic acid, to form a product of the formula

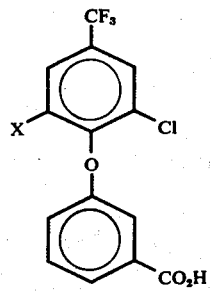

wherein X is as defined above, and
 d. reacting the product of (c) with a nitrating agent.

4. The method of claim 3 wherein X is hydrogen and Y is chlorine.

5. A method for preparing a compound of the formula

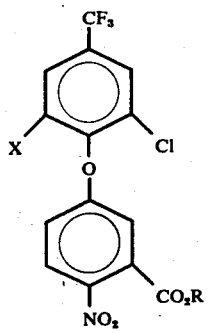

wherein R is a hydrogen atom or a ($C_1$–$C_4$) alkyl group, and X is a hydrogen atom or a chlorine atom, which comprises
 a. reacting 3-hydroxybenzoic acid with at least two equivalents of an inorganic base to form the disalt of the 3-hydroxybenzoic acid,
 b. reacting in a polar aprotic organic solvent the disalt with a benzotrifluoride of the formula

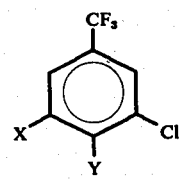

wherein Y is a chlorine atom or a fluorine atom and X is as defined above, to form a salt of an acid of the formula

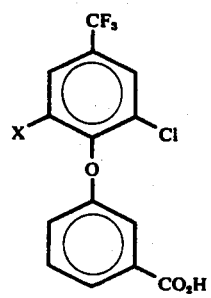

wherein X is as defined above, c. optionally acidifying the product of (b) with a strong inorganic acid, to form the acid,
d. esterifying the salt of (b) or the acid of (c) with a $(C_1-C_4)$ alkanol,
e. reacting the product of (d) with a nitrating agent, and
f. when R is a hydrogen atom, hydrolyzing the product of (e).

6. The method of claim 5 wherein X is hydrogen and Y is chlorine.

7. The method of claim 6 wherein R is a $(C_1-C_4)$ alkyl group.

8. The method of claim 7 wherein the acid of (c) is esterified with a $(C_1-C_4)$ alkanol.

9. The method of claim 6 wherein R is a hydrogen atom.

10. A method for preparing a salt of a compound of the formula

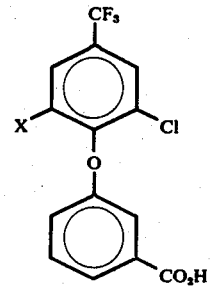

wherein X is a hydrogen atom or a chlorine atom, which comprises reacting in a polar aprotic organic solvent a disalt of 3-hydroxybenzoic acid with a benzotrifluoride of the formula

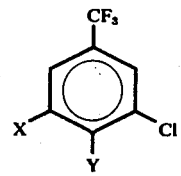

wherein Y is a chlorine atom or a fluorine atom, and X is as defined above.

* * * * *